(12) United States Patent
Ambati

(10) Patent No.: US 7,816,497 B2
(45) Date of Patent: Oct. 19, 2010

(54) COMPOSITIONS AND METHODS FOR INHIBITING DRUSEN COMPLEMENT COMPONENTS C3A AND C5A FOR THE TREATMENT OF AGE-RELATED MACULAR DEGENERATION

(75) Inventor: Jayakrishna Ambati, Lexington, KY (US)

(73) Assignee: University of Kentucky, Lexington, KY (US)

( * ) Notice: Subject to any disclaimer, the term of this patent is extended or adjusted under 35 U.S.C. 154(b) by 931 days.

(21) Appl. No.: 11/199,374

(22) Filed: Aug. 9, 2005

(65) Prior Publication Data

US 2006/0067935 A1    Mar. 30, 2006

Related U.S. Application Data

(63) Continuation-in-part of application No. 10/685,705, filed on Oct. 16, 2003, now Pat. No. 7,595,430.

(60) Provisional application No. 60/422,096, filed on Oct. 30, 2002.

(51) Int. Cl.
  C07K 16/00    (2006.01)
  C12P 21/08    (2006.01)
(52) U.S. Cl. ................................. 530/387.9; 530/391.3
(58) Field of Classification Search .................. None
  See application file for complete search history.

(56) References Cited

OTHER PUBLICATIONS

Werfel et al. (2000) Activated human T lymphocytes express a functional C3a receptor. J. of Immunol. 165: 6599-6605.*
Zwirner et al. (1999) Evaluation of C3a receptor expression on human leucocytes by the use of novel monoclonal antibodies. Immunology 97: 166-172.*
Ambati, et al. "An animal model of age-related macular degeneration in senescent macrophage recruitment impaired mice," Abstracts of the Annual Meeting of the Association for Research in Vision and Ophthamology, May 4, 2003, Database Dialog, Biosis No. 2003005125464, Abstract No. 1718.
Grossniklaus et al., "Marcrophage and retinal pigment epithelium expression of angiogenic cytokines in choroidal neovascularization," Molecular Vision, Apr. 21, 2002, pp. 119-126, vol. 8, No. 15.
Lu, Bao., et al, "Abnormalities in Monocyte Recruitment and Cytokine Expression in Monocyte Chemoattractant Protein 1-deficient Mice." J. Exp. Med, Feb. 16, 1998, vol. 187(4), pp. 601-608, ISSN 0022-1007.
Kuziel, William, A.., et al. "Severe reduction in leukocyte adhesion and monocyte extravasation in mice deficient in CC Chemokine receptor 2." Proceeding of the National Academy of the Sciences, USA, vol. 94, No. 22, Oct. 1997, pp. 12053-12058.
Raisler, Brian J., et al. "Adeno-associated virus type-2 expression of pigmented epithelium-derived factor or Kringles 1-3 of angiostatin reduce retinal neovascularization." PNAS, Jun. 25, 2002, vol. 99, No. 13, pp. 8909-8914.
Acland, Gregory, M., et al. "Gene therapy restores vision in canine model of childhood blindness." Nature Genetics, vol. 28, May 2001, pp. 92-95.
Elner, Victor, M., et al. "Cell-Associated Human Retinal Pigment Epithelium Interleukin-8 and Monocyte Chemotactic Protein-1: Immunochemical and In-situ Hybridization Analyses." Experimental Eye Research, Dec. 1997, vol. 65, No. 6, pp. 781-789.
Doetschman, T. (1999) Interpretation of phenotype in genetically engineered mice. Laboratory Animal Science 49(2): 137-143.
Donehower et al. (1995) Effects of genetic background on tumorigenesis in p53-deficient mice. Molecular Carnicogenesis 14: 16-22.
Jacks et al. (1992) Effects of an Rb mutation in the mouse. Nature 359: 295-300.
Jaenisch et al. (1988) Transgenic Animals. Science 240: 1468-1474.
Kuehn et al. (1987) A potential animal model for Lesch-Nyhan syndrome through introduction of HPRT mutations into mice. Nature 326: 295-298.
Moens et al. (1993) Defects in heart and lung development in compound heterozygotes for two different targeted mutations at the N-Myc locus. Development 119: 485-499.
Petridou et al. (2003) Heterogeneous inducible mammary-specific expression of JAB/SOCS1 in lactating transgenic mice is associated with no obvious phenotype, even at the cellular level. Transgenic Research 12: 693-706.
Sigmund, CD (2000) Viewpoint: Are studies in genetically altered mice out of control? Arterioscler. Thromb. Vasc. Biol. 20: 1425-1429.
United States Office Action issued in U.S. Appl. No. 10/685,705, dated Oct. 12, 2006.

* cited by examiner

*Primary Examiner*—Anne-Marie Falk
(74) *Attorney, Agent, or Firm*—McDermott Will & Emery LLP

(57) ABSTRACT

Activated C3 (C3a) and its receptor (C3aR) and activated C5 (C5a) and its receptor (C5aR) have been shown to induce vascular endothelial growth factor (VEGF) expression in vitro and in vivo. Compositions and methods for inhibiting C3a, C3aR, C5a and C5aR for the treatment and/or prevention of neovascular disease are provided. Also provided are Novel therapeutic targets and diagnostic markers for choroidal neovascularization.

5 Claims, 6 Drawing Sheets

COMPOSITIONS AND METHODS FOR INHIBITING DRUSEN COMPLEMENT COMPONENTS C3A AND C5A FOR THE TREATMENT OF AGE-RELATED MACULAR DEGENERATION

This application is a continuation-in-part to U.S. patent application Ser. No. 10/685,705 filed Oct. 16, 2003 now U.S. Pat. No. 7,595,430 which claims priority to U.S. provisional application Ser. No. 60/422,096, filed Oct. 30, 2002, each of which are incorporated herein in their entirety.

GOVERNMENT SUPPORT

This invention was made with government support under grant numbers: (1) NIH EY015422 awarded by the National Eye Institute of the National Institutes of Health (NEI/NIH), (2) 5T32DC000065 (training grant) awarded by the National Institute on Deafness and Other Communication Disorders of the National Institutes of Health (NIDCD/NIH), (3) NIH GM62134 awarded by the NIH, and (4) NIH GM069736 awarded by the NIH. The government has certain rights in the invention.

FIELD OF THE INVENTION

This invention relates to compositions and methods for treating and/or preventing age-related macular degeneration (AMD). More particularly, the invention relates to the use of antagonists and antibodies to activated complement component 3 (C3a) and/or its receptor (C3aR), and activated complement components 5 (C5a) and/or its receptor (C5aR) to reduce vascular endothelial growth factor (VEGF) expression and inhibit choroidal neovascularization (CNV). This invention also relates to an assay for the detection of C3a, C3aR, C5a and/or C5aR as a predisposition for and/or early detection of AMD.

BACKGROUND OF THE INVENTION

Age-related macular degeneration (AMD) is the leading cause of permanent vision loss among the elderly in many industrialized countries. Smith, W., Assink, J., Klein, R., Mitchell, P., Klayer, C. C., Klein, B. E., Hofman, A., Jensen, S., Wang, J. J. & de Jong, P. T. (2001) *Ophthalmology* 108, 697-704. The majority of vision loss due to AMD is a result of pathologic new blood vessels, termed CNV, invading the retina from the underlying choroid through fractures in Bruch membrane, the extracellular matrix between the choroid and the retinal pigment epithelium (RPE). The earliest clinical hallmark of AMD is the appearance of drusen (Gass, J. D. (1972) *Trans Am Ophthalmol Soc* 70, 409-36), localized lipoproteinaceous deposits between the RPE and Bruch membrane. Although their presence is an epidemiological risk factor for the development of CNV (Bressler, S. B., Maguire, M. G., Bressler, N. M. & Fine, S. L. (1990) *Arch Ophthalmol* 108, 1442-7; and Macular Photocoagulation Study Group (1997) *Arch Ophthalmol* 115, 741-7), the mechanism of how, or if, drusen provoke CNV remains undefined. Some investigators have suggested that drusen are epiphenomena, while others have claimed that drusen constituents act as a focal stimulus for inflammatory cells that secrete angiogenic molecules such as VEGF, and still others have suggested that drusen disturb RPE homeostasis by impairing transport across Bruch membrane. Reviewed in Ambati, J., Ambati, B. K., Yoo, S. H., Ianchulev, S. & Adamis, A. P. (2003) *Surv Ophthalmol* 48, 257-293.

Recent work has demonstrated that complement components C3 and C5 are principal constituents of drusen in patients with AMD. Mullins, R. F., Russell, S. R., Anderson, D. H. & Hageman, G. S. (2000) *FASEB J* 14, 835-46; Johnson, L. V., Ozaki, S., Staples, M. K., Erickson, P. A. & Anderson, D. H. (2000) *Exp Eye Res* 70, 441-9; Anderson, D. H., Mullins, R. F., Hageman, G. S. & Johnson, L. V. (2002) *Am J Ophthalmol* 134, 411-31; and Leitner, W. P., Staples, M. K. & Anderson, D. H. (2001) *Exp Eye Res* 73, 887-96. Their presence as well as that of the membrane-attack-complex (MAC) C5b-9 and other acute phase reactant proteins in RPE cells overlying drusen has fueled speculation that drusen biogenesis involves chronic inflammatory processes that either can trigger complement activation and formation of MAC acting to lyse RPE cells or disturb physiological homeostasis in RPE cells. Johnson, L. V., et al. (2001) *Exp Eye Res* 73, 887-96.

Recently we described an animal model of AMD in aged $Ccl2^{-/-}$ and $Ccr2^{-/-}$ mice, which develop many salient pathological features seen in the human condition. Ambati, J., Anand, A., Fernandez, S., Sakurai, E., Lynn, B. C., Kuziel, W. A., Rollins, B. J. & Ambati, B. K. (2003) *Nat Med* 9, 1390-1397. Interestingly, RPE and choroidal deposits of C3 and C5 also are found in these mice at a young age. The inability of these mice, which are impaired in induced macrophage trafficking, to clear these complement deposits is thought to promote the later development of CNV via upregulation of RPE cell secretion of VEGF. Id. These findings suggest a mechanistic link between deposition of complement components in drusen and the development of CNV.

There is growing evidence that complement components are more than mere mediators of innate immunity. To date, their influence on the molecular regulation of angiogenesis in vivo has not been addressed. Because drusen predispose to and predate CNV, we explored whether C3a and C5a (the activated forms) play a role in CNV development by studying their impact on VEGF expression, and also in laser-induced CNV, an accelerated model of neovascular AMD that reproduces much of the pathology and immunophenotype of human CNV (Reviewed in Ambati, J., et al. (2003) *Surv Ophthalmol* 48, 257-293), using mice deficient in receptors for C3a or C5a. The effect of modulating C3a and C5a reveals novel therapeutic strategies to modulate angiogenesis in the setting of inflammation and highlights the importance of developing the ability to assay expression of markers such as C3a and C5a to for diagnostics and to target therapeutics more specifically.

SUMMARY OF THE INVENTION

In one aspect of the invention there is provided compositions for treating and/or preventing AMD. In one embodiment there are ophthalmic compositions for treating and/or preventing CNV comprising one or more of, an inactivating agent that binds selectively to C3a and/or its receptor (C3aR), an inactivating agent to C5a and/or its receptor (C5aR), or a combination thereof. In a preferred embodiment the one or more inactivating agent is an antagonist to C3a, C3aR, C5a, C5aR, or a combination thereof. In another preferred embodiment, the one or more inactivating agent is an antibody. In still another preferred embodiment, the compositions further comprise one or more pharmaceutical agent operatively attached to the inactivating agent. In another aspect of the invention there is provided methods of using the compositions described herein to inhibit VEGF expression; to inhibit CNV; to prevent and/or treat AMD.

In another aspect of the invention there is provided methods for treating and/or preventing AMD. In one embodiment there are methods for treating and/or preventing CNV comprising administering to the eye of a subject a therapeutically effective amount of a composition comprising one or more of, an inactivating agent that binds selectively to C3a, C3aR, C5a, C5aR, or a combination thereof. In a preferred embodiment the one or more inactivating agent is an antagonist to C3a, C3aR, C5a, C5aR or a combination thereof. In another preferred embodiment, the one or more inactivating agent is an antibody. Preferably, administration of such one or more antagonist or antibody to C3a, C3aR, C5a or C5aR reduces VEGF expression. In still another preferred method, the inactivating agent is operatively attached to one or more pharmaceutical agent, having therapeutic or toxic effects.

In another aspect of the invention there is provided methods, assays and kits for detecting the presence of C3a, C3aR, C5a and/or C5aR for diagnostic and treatment purposes. In a preferred embodiment, one or more of, an antibody to C3a, C3aR, C5a, C5aR, or a combination of both is introduced to the eye or to a sample from the eye of a patient and the presence of C3a, C3aR, C5a and/or C5aR is detected. Preferably, antibody is labeled with a detectable label. Examples of such detectable labels include those that are, for example, radioactive, fluorescent, chemiluminescent or absorbant-based, or a combination of the foregoing. The presence of C3a, C3ar, C5a, C5aR or a combination thereof is detected by determining whether an antibody binds selectively to a component of the eye. Detection or increased level of C3a, C3aR, C5a and/or C5aR in comparison to levels of a sample from a normal subject is indicative of a predisposition for or neovascular disease, like AMD.

DETAILED DESCRIPTION OF THE INVENTION

Figure 1:
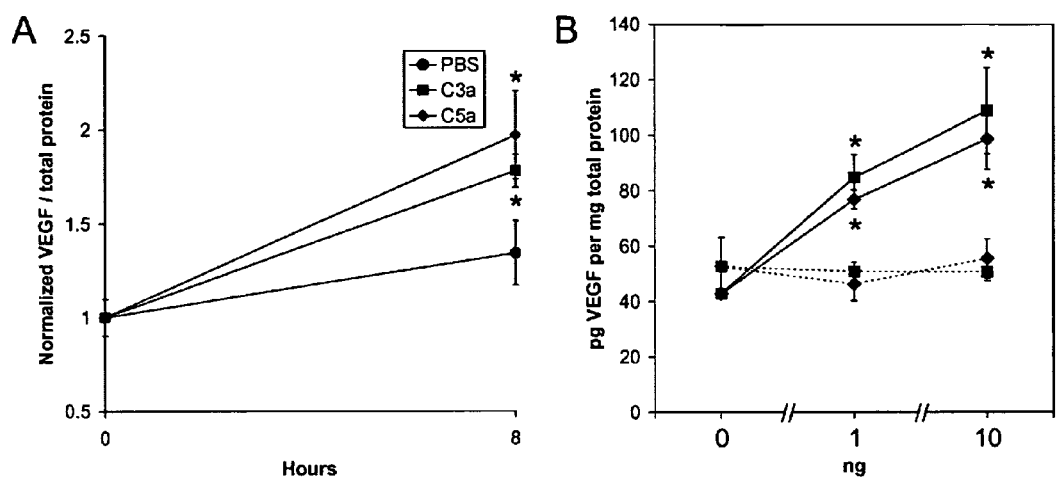
FIG. 1 (A-B). C3a and C5a upregulate VEGF in vitro and in vivo. Human C3a (50 ng/ml) and C5a (50 ng/ml) upregulated human RPE cell secretion of VEGF (A). Intravitreous injection of human C3a or C5a increase VEGF levels in the RPE/choroid (solid lines) but not in the neurosensory retina (dotted lines) in a dose-dependent fashion 4 hours after injection (B). *P<0.05 compared to PBS (A) and to 0 ng (B).

All publications, patents and patent applications cited herein, whether supra or infra, are hereby incorporated by reference in their entirety.

As used herein, the term "antagonist" means any molecule that binds to certain proteins (e.g., receptors, enzymes) at a specific (active) site on that protein, which binding suppresses, inhibits, impedes or neutralizes the activity (function) or effect of the protein.

As used herein, the terms "bind", "binding" or "bound" mean any interaction, whether via direct or indirect means, which binds, combines, couples, links, or unites molecules by means of reactive groups, either in the molecules per se or in a chemical added for that purpose, as in the affects of, for example, a specified protein, receptor or protein/receptor subunit, antibody-antigen interaction, covalent binding, and any non-covalent binding including disulfide bonds, Vanderwaals, electrostatic force, and hydrostatic force.

As used herein, the term "binds selectively to" means that the inactivating agent, including antagonists, antibodies, compounds, compositions, formulation, nucleic acids, etc., binds to one or more of C3a, C3aR, C5a, or C5aR.

As used herein, the term "detectable label(s)" are compounds or elements that can be detected due to their specific functional properties, or chemical characteristics, the use of which allows the component to which they are operatively attached to be detected, and further quantified if desired.

As used herein, the term "diagnostically effective" means that the amount of detectably labeled compound, such as monoclonal antibody or other compound, is administered in sufficient quantity to enable detection of C3a, C3aR, C5a and/or C5aR for which the antibodies or compounds are specific.

As used herein, the term "expression" means the detectable effect of a gene, like a nucleic acid sequence encoding VEGF. The term "express" means to manifest the detectable effect of a gene. A gene may be expressed inside a cell, on the surface of a cell or be secreted by the cell.

As used herein, the term "inactivate" refers to the act of inhibiting, preventing, suppressing or neutralizing C3a, C3aR, C5a and/or C5aR function to induce VEGF expression.

As used herein the term "inactivating agent" encompasses a group of functionally or structurally related proteins or small molecules, compounds or antibodies that modulate, bind to, and/or inactivate C3a, C3aR, C5a and/or C5a, and/or prevent C3a, C3aR, C5a and/or C5aR from inducing VEGF expression. Preferably, toxic side-effects are minimized. By "inactivating" it is meant that the agent may functionally inhibit, prevent, neutralize or suppress, C3a, C3aR, C5a and/or C5aR activity (function) that leads to VEGF expression.

As used herein, the term "introducing" means any means of delivery or administration, whether in vivo or in vitro, including simple contact.

As used herein, the term "neovascular disease" refers to age-related macular degeneration (AMD), including wet AMD (classic, occult, subfoveal, extrafoveal, juxtafoveal) and dry AMD, cancer, choroidal neovascularization, corneal neovascularization, cystoid macular edema, diabetic retinopathy, diabetic macular edema (DME), inflammatory or mechanical macular degeneration, iris neovascularization, myopic macular degeneration, macular degeneration due to histoplasmosis or angioid streaks or inherited retinal or choroidal dystrophies/degenerations, proliferative diabetic retinopathy, psoriasis, retinal neovascularization, vitreal neovascularization, branch/central retinal vein occlusion, retinopathy of prematurity, rheumatoid arthritis, uveitis, or infection.

As used herein, the term "neovascularization" means proliferation of blood vessels in tissue not normally containing them, or proliferation of blood vessels of a different kind than usual in tissue. Non-limiting examples of ocular neovascularization include neovascularization of the choroid (including, classic, occult, Type 1, and Type 2 choroidal), cornea, iris, retina, retinal pigmented epithelium (RPE), and/or vitreous. Ocular neovascularization is also associated with eye neovascular disease such as, for example, AMD, choroidal neovascularization, cystoid macular edema, DME, diabetic retinopathy, inflammatory diabetic retinopathy, retinopathy of prematurity, and traumatic eye injury.

As used herein, the term "operatively attached" means association with, or attachment, conjugation, linking, or binding (direct or indirect by use of another molecule, linker, etc.) of one molecule, including compounds, labels and ligands, amino acid sequence, or nucleic acid sequence, to another molecule in such a way as to allow each of the molecules to function in their intended manners.

As used herein, the term "patient" includes members of the animal kingdom including but not limited to human beings.

The inventor has discovered that significant quantities of complement components C3 and C5 are present within the RPE/choroid soon after laser injury, and that laser-induced CNV is significantly reduced in C3aR$^{-/-}$ and C5aR$^{-/-}$ mice via concerted suppression of leukocyte recruitment and VEGF expression. The inventor has also demonstrated that C3a and C5a upregulate RPE/choroid production of VEGF in the uninjured eye in a dose-dependent manner, consistent with their ability to upregulate RPE cell secretion of VEGF in vitro, and that VEGF upregulation induced by laser injury is abrogated in C3aR$^{-/-}$ and C5aR$^{-/-}$ mice.

In disease states such as AMD where the integrity of the RPE cell monolayer is compromised in some but not all regions, RPE cells would be expected to exist both confluent (quiescent) and subconfluent (proliferating) conditions. In both conditions the inventor discovered that C3a and C5a induced VEGF in RPE cells. Both C3a and C5a upregulated the secretion of VEGF by human RPE cells, both in confluent and subconfluent conditions (FIG. 1A), but not in human choroidal endothelial cells (CEC; data not shown) in vitro, confirming a previous observation about the effect of C5a. Ambati, J., Anand, A., Fernandez, S., Sakurai, E., Lynn, B. C., Kuziel, W. A., Rollins, B. J., Ambati, B. K. (2003) *Nat Med* 9, 1390-1397. This response was preserved in vivo as intravitreous injection of C3a or C5a in wild-type mice upregulated VEGF expression in the RPE/choroid in a dose-dependent fashion within 4 hours of administration (FIG. 1B). The absence of a similar effect in the neurosensory retina demonstrated that VEGF upregulation was not a non-specific response to intraocular injection.

Figure 2:
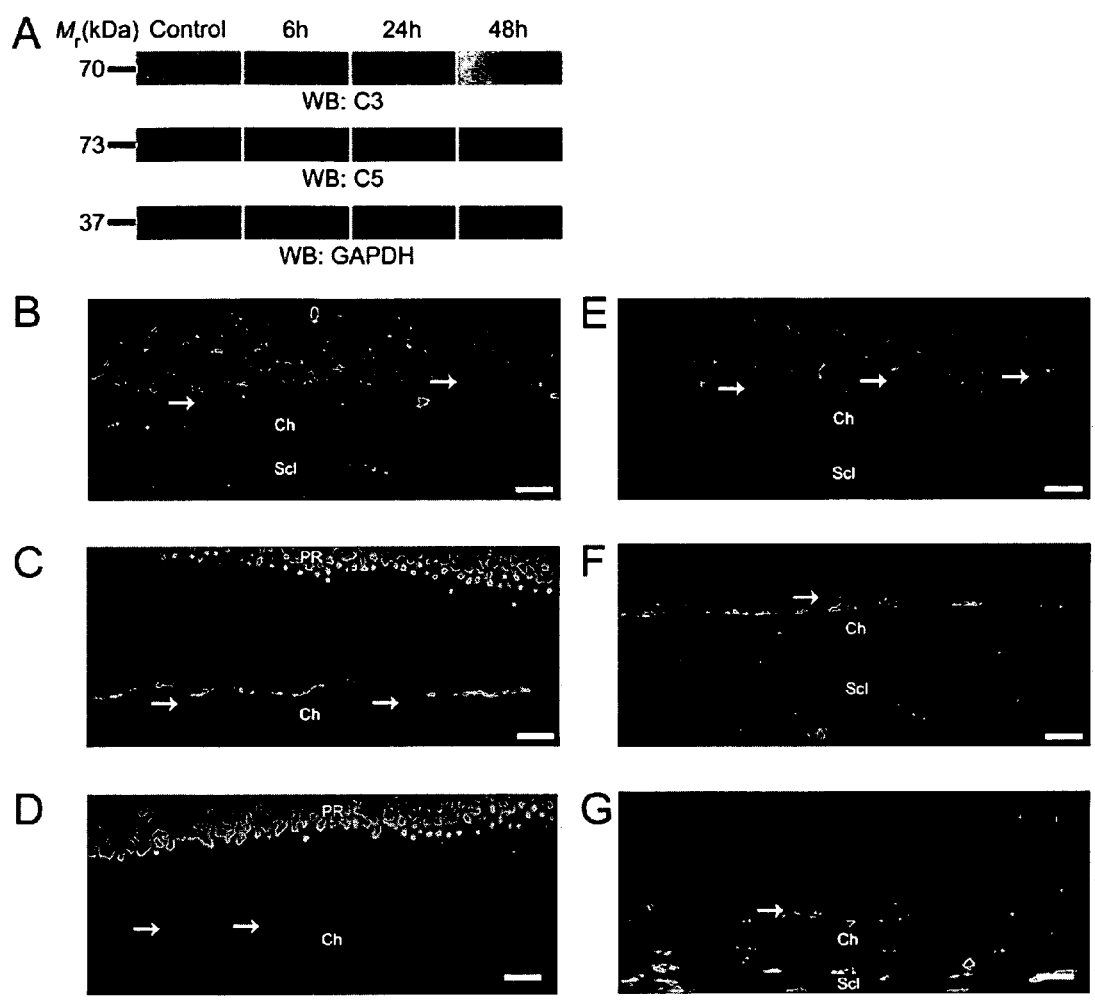
FIG. 2 (A-G). Laser injury induces C3 and C5 deposition. Western blotting shows increasing levels of C3 and C5 in the RPE/choroid of wild-type mice within 6 hours of injury and is sustained for at least 24 hours (A). C5 (B,C,D) and C3 (E,F,G) are deposited (red) in the RPE cell layer and on the apical surface of RPE cells in the area of injury (B,E) and next to the area of injury (C,F) 12 hours after injury, but not in uninjured areas (D,G). Arrows show RPE cell nuclei. Ch=choroid, PR=photoreceptor nuclei, Scl=sclera. Scale bar 20 μm.

In the laser injury model, the initial rise in VEGF levels occurred prior to the infiltration of leukocytes (Sakurai, E., Anand, A., Ambati, B. K., van Rooijen, N. & Ambati, J. (2003) *Invest Ophthalmol Vis Sci* 44, 3578-85), suggesting that resident cells such as CEC and RPE cells are responsible. There was no increase in the number of macrophages or neutrophils in the choroid 4 hours after intravitreous injection of C3a or C5a, indicating that the increase in VEGF expression was due to resident cells (data not shown). C3 and C5 expression was detected by western blotting in the RPE/choroid within 6 hours of injury, which persisted for at least 24 hours (FIG. 2A). Immunostaining revealed significant amounts of C3 and C5 deposition in and near RPE cells in the area of injury (FIGS. 2B,E). RPE cells adjacent to the site of injury also stained for C3 and C5, while uninjured areas exhibited minimal if any staining for these complement components (FIGS. 2C,D,F,G). The absence of an effect of C3a or C5a on CEC in vitro corresponded with the negligible staining of C3 or C5 in the choroid following laser injury. The peak of the VEGF response 3 days after injury parallels the infiltration of macrophages and can be blunted by macrophage depletion, suggesting that it is these recruited cells that are responsible for the second surge in VEGF.

The inventor has found that there is no significant increase in VEGF levels at any time point in C3aR$^{-/-}$ and C5aR$^{-/-}$ mice following injury. VEGF levels in the RPE/choroid one day after injury were significantly reduced in C3aR$^{-/-}$ (48.6%±7.5%; P=0.06) and C5aR$^{-/-}$ mice (55.4%±3.1%; P=0.04) compared to wild-type mice. The lack of an initial rise in VEGF immediately after injury in these animals is attributed to the disruption of C3a and C5a induced VEGF.

Figure 3:
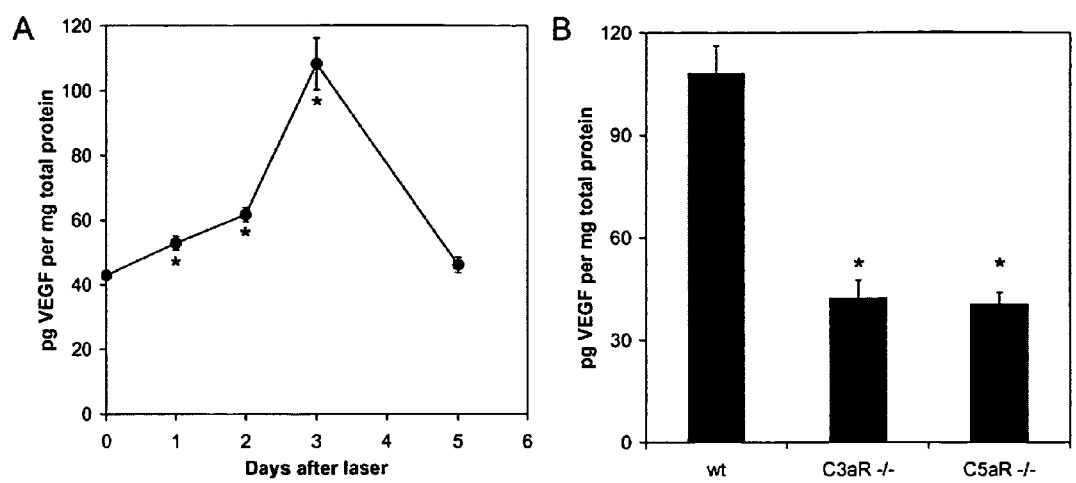
FIG. 3 (A-B). Laser-induced VEGF induction is diminished in C3aR$^{-/-}$ and C5aR$^{-/-}$ mice. VEGF levels in the RPE/choroid, which peak 3 day after laser injury (A) are significantly reduced in both knockout strains (B). *P<0.05 compared to level before injury (A) and to wild-type (wt) mice (B).

Reduced VEGF levels persisted even 3 days after injury (FIG. 3A), the time point of the peak of the VEGF response (Sakurai, E., Anand, A., Ambati, B. K., van Rooijen, N. & Ambati, J. (2003) *Invest Ophthalmol Vis Sci* 44, 3578-85), in C3aR$^{-/-}$ (60.9%±4.9%; P=0.01) and C5aR$^{-/-}$ mice (62.5%±3.1%; P=0.004) compared to wild-type mice (FIG. 3B). The peaks of VEGF in C3aR$^{-/-}$ and C5aR$^{-/-}$ mice following laser injury were not elevated above pre-injury levels in wild-type mice (P=0.99). The missing secondary surge in VEGF in C3aR$^{-/-}$ and C5aR$^{-/-}$ mice might be due both to the interference with complement component receptor mediated signaling and also the reduction in leukocyte recruitment.

Figure 4:
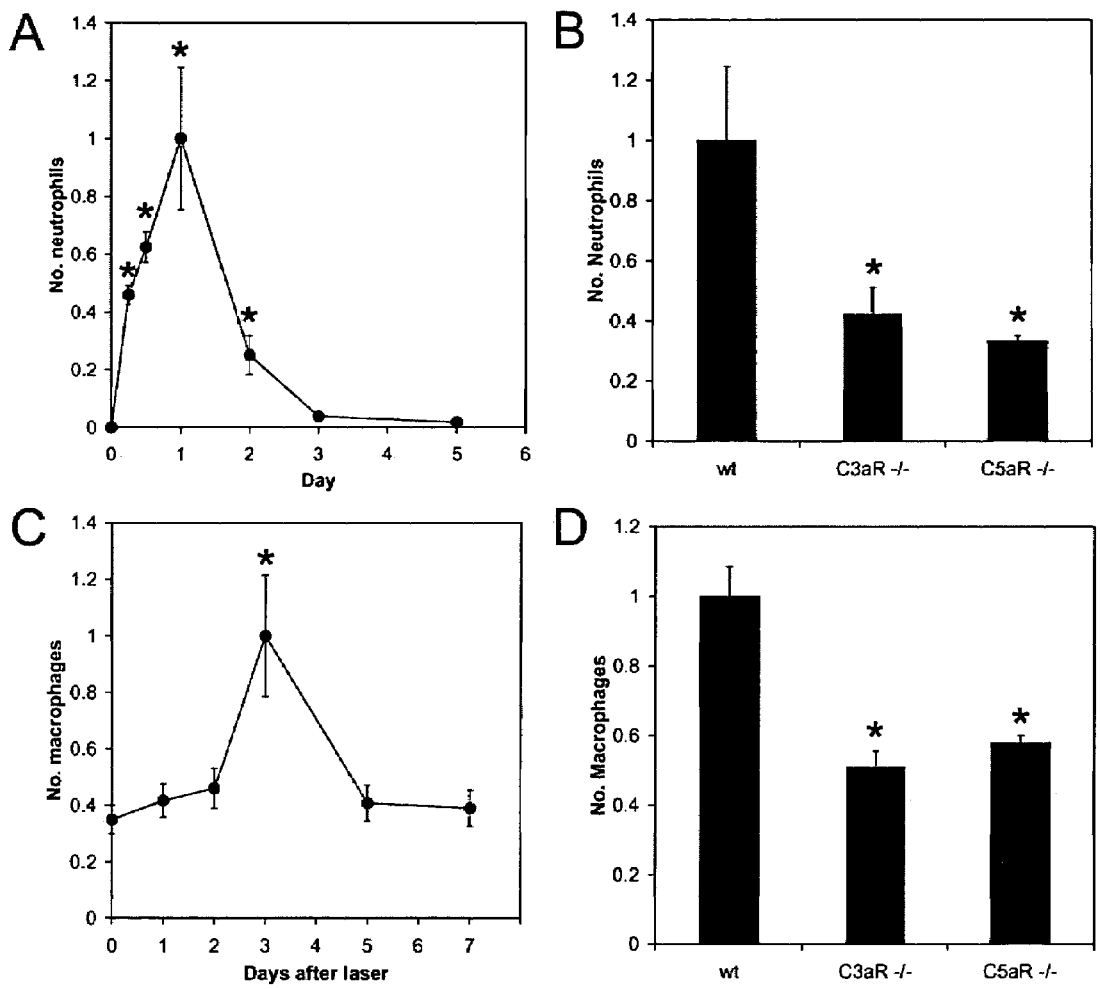
FIG. 4 (A-D). Leukocyte recruitment to the choroid is diminished in C3aR$^{-/-}$ and C5aR$^{-/-}$ mice. Neutrophil infiltration (normalized to peak), which peaks 1 day after laser injury (A) is significantly reduced in both knockout strains (B). Macrophage infiltration (normalized to peak), which peaks 3 days after laser injury (C) is significantly reduced in both knockout strains (D). *P<0.05 compared to number of cells before injury (A,C) and to wild-type (wt) mice (B,D).

Leukocyte recruitment, which plays a pivotal role in laser-induced CNV (Sakurai, E., Taguchi, H., Anand, A., Ambati, B. K., Gragoudas, E. S., Miller, J. W., Adamis, A. P. & Ambati, J. (2003) *Invest Ophthalmol Vis Sci* 44, 2743-9; and Sakurai, E., Anand, A., Ambati, B. K., van Rooijen, N. & Ambati, J. (2003) *Invest Ophthalmol Vis Sci* 44, 3578-85), was also markedly reduced in C3aR$^{-/-}$ and C5aR$^{-/-}$ mice following injury. The peak of neutrophil infiltration into the choroid, which occurred 1 day after injury (FIG. 4A), was reduced in C3aR$^{-/-}$ (57.8%±9.0%; P=0.05) and C5aR$^{-/-}$ mice (66.6%±1.7%; P=0.02) compared to wild-type mice (FIG. 4B). The peak of macrophage infiltration into the choroid, which occurred 3 days after injury (FIG. 4C), was reduced in C3aR$^{-/-}$ (49.1%±4.6%; P=0.04) and C5aR$^{-/-}$ mice (42.1%+ 2.1%; P=0.05) compared to wild-type mice (FIG. 4D). This may be due to direct interception of the chemotactic function of C3aR and C5aR on leukocytes or reduction in VEGF, which itself is a chemoattractant. Barleon, B., Sozzani, S., Zhou, D., Weich, H. A., Mantovani, A. & Marme, D. (1996) *Blood* 87, 3336-43; and Clauss, M., Weich, H., Breier, G., Knies, U., Rockl, W., Waltenberger, J. & Risau, W. (1996) *J Biol Chem* 271, 17629-34. It also may result from indirect reduction of chemokines such as Ccl-2 and Cxcl-2, which the inventor and others have shown can be induced by complement components. Ambati, J., Anand, A., Fernandez, S., Sakurai, E., Lynn, B. C., Kuziel, W. A., Rollins, B. J. &

Ambati, B. K. (2003) *Nat Med* 9, 1390-1397; Fukuoka, Y., Strainic, M. & Medof, M. E. (2003) *Clin Exp Immunol* 131, 248-53; Czermak, B. J., Sarma, V., Bless, N. M., Schmal, H., Friedl, H. P. & Ward, P. A. (1999) *J Immunol* 162, 2321-5; and Laudes, I. J., Chu, J. C., Huber-Lang, M., Guo, R. F., Riedemann, N. C., Sarma, J. V., Mahdi, F., Murphy, H. S., Speyer, C., Lu, K. T., Lambris, J. D., Zetoune, F. S. & Ward, P. A. (2002) *J Immunol* 169, 5962-70.

While RPE cells constitutively produce both Ccl-2 (Elner, V. M., Burnstine, M. A., Strieter, R. M., Kunkel, S. L. & Elner, S. G. (1997) *Exp Eye Res* 65, 781-9; and Holtkamp, G. M., De Vos, A. F., Peek, R. & Kijlsta, A. (1999) *Clin Exp Immunol* 118, 35-40) and VEGF (Adamis, A. P., Shima, D. T., Yeo, K. T., Yeo, T. K., Brown, L. F., Berse, B., D'Amore, P. A. & Folkman, J. (1993) *Biochem Biophys Res Commun* 193, 631-8), the stimuli inducing their overexpression in human CNV (Grossniklaus, H. E., Ling, J. X., Wallace, T. M., Dithmar, S., Lawson, D. H., Cohen, C., Elner, V. M., Elner, S. G. & Sternberg, P., Jr. (2002) *Mol Vis* 8, 119-26; Frank, R. N., Amin, R. H., Eliott, D., Puklin, J. E. & Abrams, G. W. (1996) *Am J Ophthalmol* 122, 393-403; and Lopez, P. F., Sippy, B. D., Lambert, H. M., Thach, A. B. & Hinton, D. R. (1996) *Invest Ophthalmol Vis Sci* 37, 855-68) are unknown. The demonstration that C3a and C5a can trigger Ccl-2 and VEGF production make them attractive candidates as markers and modulators of CNV given their presence in drusen deposits in patients with AMD and in a mouse model of AMD, as well as following laser injury, particularly because they can be locally synthesized in the RPE. Mullins, R. F., et al. (2000) *FASEB J* 14, 835-46; and Johnson, L. V., et al. (2000) *Exp Eye Res* 70, 441-9.

By intercepting specific receptor-mediated pathways, the inventor has identified a novel mechanistic association between the complement and cytokine networks in promoting laser-induced CNV. These findings introduce the C3a and C5a complement factors as modulators of angiogenesis in the eye. These findings also translate into functional inhibition.

Figure 5:
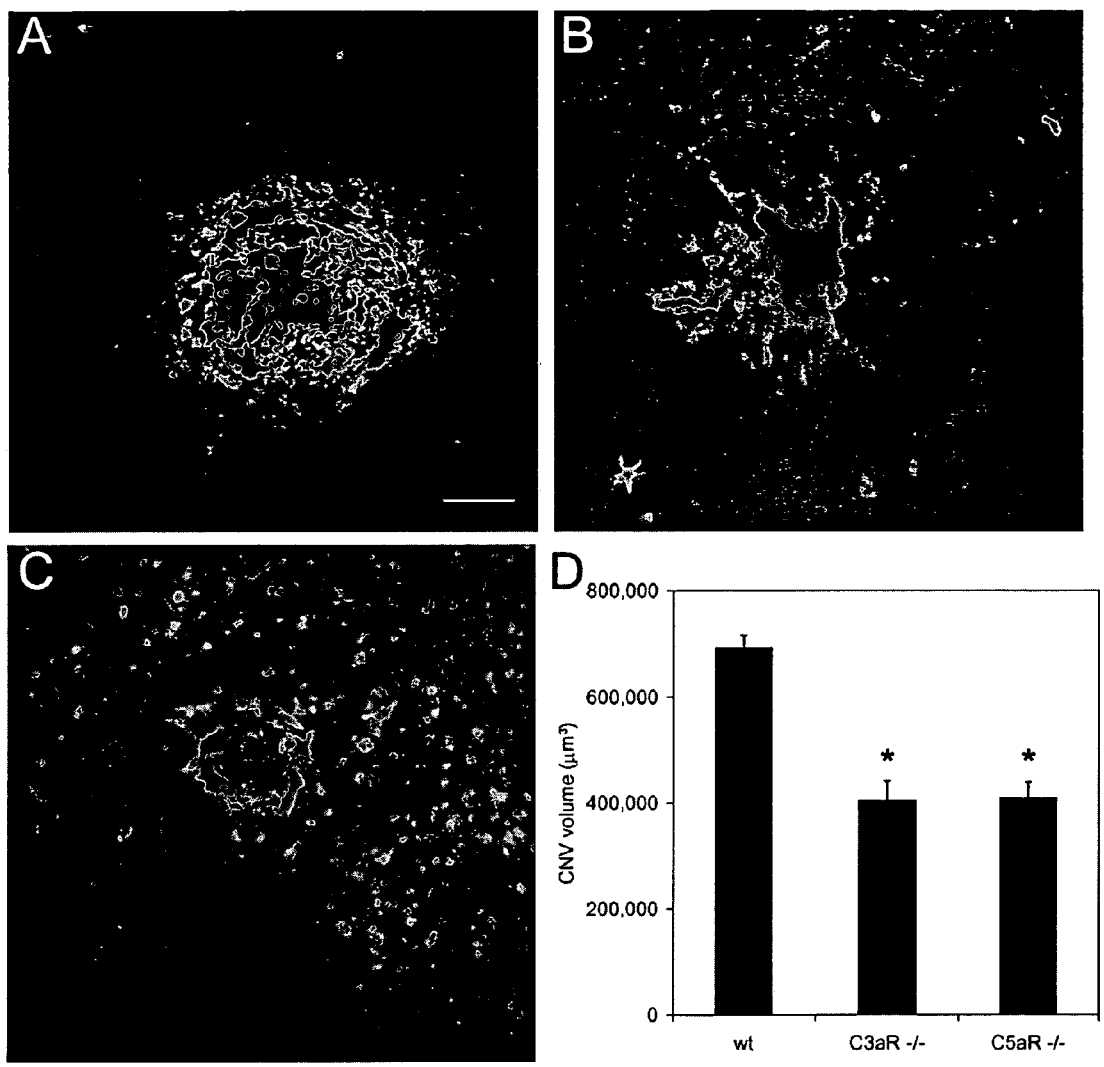
FIG. 5 (A-D). CNV is reduced in knockout mice. Stacked confocal images (1 μm sections) of FITC-isolectin B4 labeled tissue within laser scars in wild-type (A), C3aR$^{-/-}$ (B) and C5aR$^{-/-}$ (C) mice demonstrate more than 40% reduction in CNV volume (D). *P<0.05 compared to wild-type (wt) mice. Scale bar 100 μm.
Figure 6:
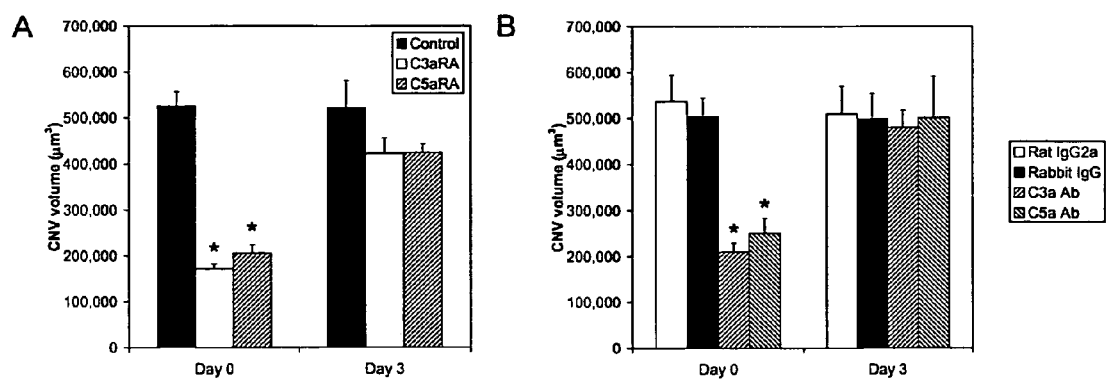
FIG. 6 (A-B). (A) CNV is reduced in wild-type mice treated with C3aRA or C5aRA compared with control peptide, only if injected immediately after laser injury. (B) CNV is reduced in wild-type mice treated with neutralizing anti-C3a or anti-C5a antibodies compared with isotype control antibodies, only if injected immediately after laser injury.

The volume of laser-induced CNV was significantly reduced in C3aR$^{-/-}$ (41.5%±5.2%; n=13; P<0.001) and C5aR$^{-/-}$ mice (40.8%±4.3%; n=14; P<0.001) compared to wild-type mice (n=17) (FIG. 5). To complement the genetic ablation studies, the inventor tested neutralizing antibodies against C3a or C5a and peptide antagonists of their receptors in wild-type mice. CNV was significantly reduced by treatment with both peptide antagonists and both neutralizing antibodies, compared to control peptide or antibodies, if these blockers were injected immediately after laser injury but not if they were injected 3 days later (FIG. 6). These data indicate that the bulk of the pro-angiogenic effects of C3a and C5a in this model can be attributed to the very early release and deposition of these activated complement components. Suppression of CNV in C3aR$^{-/-}$ and C5aR$^{-/-}$ mice, and in wild-type mice treated with antagonists of the activated complement components or their receptors also may be due to downregulation of leukocyte-endothelial adhesion molecules, which can be promoted by C3a and C5a (Albrecht, E. A., Chinnaiyan, A. M., Varambally, S., Kumar-Sinha, C., Barrette, T. R., Sarma, J. V. & Ward, P. A. (2004) *Am J Pathol* 164, 849-859; Ross, G. D., Cain, J. A. & Lachmann, P. J. (1985) *J Immunol* 134, 3307-15; and Lo, S., Detmers, P., Levin, S. & Wright, S. (1989) *J. Exp. Med.* 169, 1779-1793) and are critical for CNV formation. Sakurai, E., et al., (2003) *Invest Ophthalmol Vis Sci* 44, 2743-9.

Compositions of the Invention

In one aspect of the invention there is provided compositions comprising C3a, C3aR, C5a, and/or C5aR inactivating agents for treating and/or preventing AMD. In a preferred embodiment there is ophthalmic compositions to treat and/or prevent choroidal neovascularization by reducing VEGF. The compositions comprise one or more of, an inactivating agent that binds selectively to C3a, C3aR, C5a, C5aR, or a combination thereof.

The inactivating agent may be an antagonist, antibody, anti-sense oligonucleotide, aptamer, miRNA, ribozyme, siRNA, or small molecule. In a preferred embodiment of this aspect of this invention, the inactivating agent is an antagonist to C3a, C3aR, C5a and/or C5aR. Non-limiting examples of an antagonist of the invention include the C3aR antagonist (C3aRA) $N^2$-[(2,2-diphenylethoxy)acetyl]-1-arginine, the C3a and C3aR antagonists disclosed in U.S. Pat. Nos. 5,942,405 and 6,489,339, the C5aR antagonist (C5aRA) AcF-[OP-dChaWR], and the C5aR antagonists disclosed in U.S. Pat. Nos. 6,916,830, 6,884,815, 6,858,637, 6,821,950, 6,777,422, 6,723,743, 6,355,255, 6,270,775, 5,846,547, 5,837,499, 5,807,824, 4,772,584, 4,692,511, or similar peptidases or a combination thereof. Methods to identify other antagonists are described in U.S. Pat. Nos. 5,861,272 and 5,614,370. Other antagonists to C3a, C3aR, C5a and/or C5a known to the skilled artisan or hereafter discovered may be used. Candidate antagonists include pharmaceutical compounds, small molecules, peptides, nucleic acids, including oligonucleotides and polynucleotides in sense or antisense orientation and aptamers.

In another preferred embodiment of this aspect of the invention, the inactivating agent is an antibody or functional antibody fragment (Fab) to C3a, C3aR, C5a and/or C5a. Preferably, the agent is an antagonist to C3a, C3aR, C5a and/or C5aR. It is also preferable that the agent is an antibody to C3a, C3aR, C5a and/or C5aR. Non-limiting examples of antibodies of the invention, include MAb anti-C3a from Quidel, San Diego, Calif. [catalog no. A203,]; anti-human C3aR antibodies hC3aRZ1 and hC3aRz2, as described in Kacani, L. et al., *J. Immunol.* (2001) 166:3410-3415; mouse anti-human C5a antibodies from Hycult Biotechnology BV of the Netherlands [clones 557, 2942 and 2952]; anti-human C5a antibody from Tanox, Inc. [137-26], as described in Fung, M. et al. *Clin Exp Immunol.* (2003) August; 133(2):160-9; C5a antibodies disclosed in U.S. Pat. No. 5,480,974; anti-EX1 human C5aR MAb S5/1, as described in Opperamann, M., et al., *J. Immunol.* (1993) October 1; 151(7):3785-94; and anti-C5aR MAb S5/1, as described in Kacani, L. et al., *J. Immunol.* (2001) 166:3410-3415. Anti-C3 and anti-C5 antibodies may also function to inhibit C3a and/or C3aR or C5a and/or C5aR, respectively, such as, for example, goat polyclonal anti-human C5 antibody from Quidel, San Diego, Calif. [catalog no. A306]. A hybridoma that produces a monoclonal anti-C3a, anti-C3aR, anti-C5a and/or anti-C5aR antibody that binds to substantially the same epitope as any of the foregoing antibodies is another aspect of the invention. The antibodies may be polyclonal antibodies or monoclonal antibodies.

Polyclonal antibodies to C3a, C3aR, C5a and C5a can be produced by various procedures well known in the art. For example, purified C3aR, preferably human C3aR, can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

The use of monoclonal antibodies (MAbs) or derivatives thereof to C3a, C3aR, C5a and/or C5aR is preferred. MAbs are recognized to have certain advantages, e.g., reproducibility and large-scale production, that makes them suitable for clinical treatment. The invention thus preferably provides monoclonal antibodies of the murine, human, monkey, rat, hamster, rabbit and even frog or chicken origin. Murine, human or humanized monoclonal antibodies will generally be preferred. Preferably the anti-C3a antibody, anti-C3aR antibody, anti-C5a antibody, and anti-C5aR antibody are neutralizing humanized rat or mouse IgG2a against human C3a, C3aR, C5a and C5a, respectively.

Monoclonal antibodies to C3a, C3aR, C5a and C5aR can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981). An exemplary antibody to C5a is described in U.S. Pat. No. 5,177,190.

The ophthalmic compositions of this invention may further comprise one or more pharmaceutical agent operatively attached to the inactivating agent. In the context of the present invention the selected pharmaceutical agent is thus targeted to the RPE/choroid area of the eye by the inactivating agent, allowing selective inhibition of C3a, C3aR, C5a and/or C5aR activity and/or treatment of an eye. The pharmaceutical agent may comprise therapeutic agents such as any compound, drug, molecule or protein having a desired therapeutic effect, including, for example, the breakdown or clearance of drusen, inhibition of CNV, inhibition of C3a, C3aR, C5a or C5aR activity and/or the inhibition of VEGF expression. Such other therapeutic agents may include anti-allergics, anti-angiogenics, anti-biotics, anti-cancer agents, anti-infectives, anti-inflammatory agents, dry eye solutions, steroids, and the like. This list is, of course, merely exemplary in that the technology for attaching pharmaceutical agents to antagonists for specific delivery to tissues is well established.

A toxin bound anti-C3a, anti-C3aR, anti-C5a, or anti-C5aR antibody of the present invention comprises immunotoxins. The preparation of immunotoxins is, in general, well known in the art (see, e.g., U.S. Pat. No. 4,340,535, and EP 4416), however, certain advantages may be achieved through the application of certain preferred technology, both in the preparation of the immunotoxins and in their purification for subsequent clinical administration. For example, while IgG based immunotoxins will typically exhibit better binding capability and slower blood clearance than their Fab' counterparts, Fab' fragment-based immunotoxins will generally exhibit better tissue penetrating capability as compared to IgG based immunotoxins.

Additionally, while numerous types of disulfide-bond containing linkers are known which can successfully be employed to conjugate the toxin moiety with the antibody inactivating agent, certain linkers will generally be preferred over other linkers, based on differing pharmacologic characteristics and capabilities. For example, linkers that contain a disulfide bond that is sterically "hindered" are to be preferred, due to their greater stability in vivo, thus preventing release of the toxin moiety prior to binding at the site of action.

Cross-linking reagents are used to form molecular bridges that tie together functional groups of two different proteins (e.g., a toxin and an inactivating agent). To link two different proteins in a step-wise manner, hetero bifunctional cross-linkers can be used which eliminate the unwanted homopolymer formation. An exemplary hetero bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., dgA).

The spacer arm between these two reactive, groups of any cross-linkers may have various lengths and chemical compositions. A longer spacer arm allows a better flexibility of the conjugate components while some particular components in the bridge (e.g., benzene group) may lend extra stability to the reactive group or an increased resistance of the chemical link to the action of various aspects (e.g., disulfide bond resistant to reducing agents).

Non-limiting examples of toxic agents to bind to anti-C3a, anti-C3aR, anti-C5a, or anti-C5aR antibodies include any chemical agents having localized cytotoxic effects and radioisotopes. Exemplary radioisotopes that can be operatively attached to an inactivating agent include α-emitters such as, for example, $^{211}$Astatine, $^{212}$Bismuth and $^{213}$Bismuth, as well as β-emitters such as, for example, $^{131}$Iodine, $^{90}$Yttrium, $^{177}$Lutetium, $^{153}$Samarium and $^{109}$Palladium. Particularly preferred radioisotopes are $^{211}$Astatine and $^{131}$Iodine. This list is, of course, merely exemplary in that the technology for attaching pharmaceutical agents to antibodies for specific delivery to tissues is well established.

The ophthalmic compositions of the present invention may still further comprise one or more anti-inflammatory agent operatively attached to an inactivating agent. The ophthalmic compositions of the present invention may contain one or more inactivating agent that binds selectively to C3a, C3aR, C5a and/or C5aR with one or a combination of a steroid drug, such as triamcinolone, fluocinolone, anacortave acetate, dexamethasone and combinations thereof; or a non-steroidal anti-inflammatory drug, such as celecoxib, flurbiprofen, and aspirin, for example.

The ophthalmic compositions of this invention may still further comprise a pharmaceutically acceptable carrier. Such pharmaceutical carriers can be sterile liquids, such as water and oils, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. Suitable pharmaceutical excipients include starch, glucose, lactose, sucrose, gelatin, malt, rice, sodium stearate, glycerol monostearate, glycerol, propylene, glycol, water, and the like. The composition, if desired, can also contain minor amounts of wetting or emulsifying agents, or pH buffering agents. The C3a and C5a inactivating agents, and any combinations thereof or other active agents of the composition may be encased in polymers or fibrin glues to provide controlled release of the active agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin. Such compositions will contain a therapeutically effective amount of one or more of the inactivating agent, preferably in purified form, together with a suitable amount of carrier so as to provide the form for proper administration to the patient. The formulation should suit the mode of administration.

Ophthalmic pharmaceutical products are typically packaged in multidose form. Preservatives are thus included to prevent microbial contamination during use. Suitable preservatives include: polyquaternium-1, benzalkonium chloride, thimerosal, chlorobutanol, methyl paraben, propyl paraben, phenylethyl alcohol, edetate disodium, sorbic acid, or other agents known to those skilled in the art. The use of polyquaternium-1 as the antimicrobial preservative is preferred. Typically such preservatives are employed at a level of from 0.001% to 1.0% by weight.

The solubility of the components of the present compositions may be enhanced by a surfactant or other appropriate co-solvent in the composition. Such co-solvents include polysorbate 20, 60, and 80, polyoxyethylene/polyoxypropylene surfactants (e.g., Pluronic F-68, F-84 and P-103), cyclodextrin, or other agents known to those skilled in the art. Typically such co-solvents are employed at a level of from 0.01% to 2% by weight.

The use of viscosity enhancing agents to provide the topical compositions of the invention with viscosities greater than the viscosity of simple aqueous solutions may be desirable to increase ocular absorption of the active compounds by the target tissues or increase the retention time in the eye. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents know to those skilled in the art. Such agents are typically employed at a level of from 0.01% to 2% by weight.

The C3a, C3aR, C5a and/or C5aR inactivating agent-containing compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the active agents of the compositions of the invention which will be effective in the treatment, inhibition and/or prevention of neovascularization of the eye can be determined by standard clinical techniques. In addition, in vitro assays may optionally be employed to help identify optimal dosage ranges. The precise dose to be employed in the formulation will also depend on the route of administration, and the seriousness of the neovascular disease or disorder, and should be decided according to the judgment of the practitioner and each patient's circumstances. Effective doses may be extrapolated from dose-response curves derived from in vitro or animal model test systems.

Methods of the Invention

In another aspect of this invention there is provided methods of treating AMD. In one embodiment there are methods for treating and/or preventing CNV comprising administering to the eye of a subject a therapeutically effective amount of the compositions described herein. Preferably, administration of such one or more antagonist or antibody to C3a, C3aR, C5a or C5aR reduces VEGF expression. In another embodiment there is a method of using the compositions described herein to The compositions may be administered together with other biologically active agents. Administration of the compositions of the invention may be systemic or local. Local administration to the affected eye(s) may be achieved by, for example, and not by way of limitation, local infusion during surgery, transscleral delivery, intravitreous injection, intracameral injection, subretinal injection, topical application, e.g., in conjunction with a wound dressing after surgery or via drops or application of a gel or other topical solution, by injection, or by means of an implant, said implant being of a porous, non-porous, or gelatinous material, including membranes, such as sialastic membranes, or fibers. Preferably, when administering a protein, including an antibody or functional fragment thereof, of the invention, care must be taken to use materials to which the protein does not absorb.

In a preferred embodiment, the composition is administered by topical application to the eye. The ophthalmic compositions are typically administered to the affected eye by applying one to four drops of a sterile solution or suspension, or a comparable amount of an ointment, gel or other solid or semisolid composition, to the surface of the affected eye one to four times per day. However, the compositions may also be formulated as irrigating solutions that are applied to the affected eye during surgical procedures.

Topical compositions will typically have a pH in the range of 4.5 to 8.0. The ophthalmic compositions must also be formulated to have osmotic values that are compatible with the aqueous humor of the eye and ophthalmic tissues. Such osmotic values will generally be in the range of from about 200 to about 400 milliosmoles per kilogram of water ("mOsm/kg"), but will preferably be about 300 mOsm/kg.

In another preferred embodiment, the composition is formulated in accordance with routine procedures as a pharmaceutical composition adapted for injection intravenously, introperitoneally, or intravitreously. In a preferred embodiment, the composition is administered by intravenous injection. A high dose intravenous immunoglobulin (IVIG), as well as F(ab)2-IVIG and even irrelevant human monoclonal antibodies all can bind C3a and C5a and interfere with their function. Basta M. et al. F(ab)'2-mediated neutralization of C3a and C5a anaphylatoxins: a novel effector function of immunoglobulins. *Nature Medicine* 2003; 9:431-8. In another preferred embodiment the composition is adapted for intravitreous injection to the eye. Typically, compositions for injection are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

A controlled release system may also be used to effect local administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105

(1989)). In yet another embodiment, a controlled release system can be placed in proximity of the eye.

Various other delivery systems are known and can be used to administer a composition of the invention, e.g., encapsulation in vesicles, liposomes, microparticles, microcapsules, recombinant cells capable of expressing the compound, receptor-mediated endocytosis (See, e.g., Wu and Wu, J. Biol. Chem. 262:4429-4432 (1987)), construction of a nucleic acid as part of a retroviral or other vector, etc. In one embodiment, the composition of the invention can be delivered in a vesicle, in particular a liposome (See Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

Diagnostics of the Invention

The present invention further provides in vitro and in vivo diagnostic methods, assays and kits. Such methods are applicable for use in generating diagnostic, prognostic or imaging information for any neovascular disease, as exemplified by age-related macular degeneration.

In one embodiments, the present invention concerns immunodetection methods for binding, purifying, removing, quantifying or otherwise generally detecting C3a, C3aR, C5a and/or C5aR and for diagnosing neovascular disease, like AMD, of the eye. The antibodies to C3a, C3aR, C5a and C5aR of the present invention may be employed to detect C3a, C3aR, C5a and/or C5aR, respectively, in vivo (see below), in isolated issue samples, biopsies or swabs and/or in homogenized tissue samples. Such immunodetection methods have evident diagnostic utility, but also have applications to non-clinical samples, such as in the titering of antigen samples, and the like.

The steps of various useful immunodetection methods have been described in the scientific literature, such as, e.g., Nakamura et al. (1987). In general, the immunobinding methods include obtaining a sample suspected of containing C3a and/or C5a and contacting the sample with C3a and/or C5a antibodies under conditions effective to allow the formation of immunocomplexes. In such methods, the antibody may be linked to a solid support, such as in the form of a column matrix, and the sample suspected of containing C3a and/or C5a will be applied to the immobilized antibody.

More preferably, the immunobinding methods include methods for detecting or quantifying the amount of C3a, C3aR, C5a and/or C5aR in a sample, which methods require the detection or quantification of any immune complexes formed during the binding process. Here, one would obtain a sample suspected of containing C3a, C3aR, C5a and/or C5aR and contact the sample with an antibody in accordance herewith and then detect or quantify the amount of immune complexes formed under the specific conditions.

The biological sample analyzed may be any sample that is suspected of containing C3a, C3aR, C5a and/or C5aR, generally from an animal or patient suspected of having an neovascular disease. The samples may be a fluid, tissue section or specimen, a biopsy, a swab or smear test sample, a homogenized tissue extract or separated or purified forms of such. A sample can be a liquid such as fluids of the eye such as tears, urine, saliva, cerebrospinal fluid, blood, serum or the like; a solid or semi-solid such as vitreous humor, tissues, feces, or the like; or, alternatively, a solid tissue such as those commonly used in histological diagnosis. Preferably, the sample is a sample from plasma, serum, or the vitreous humor, subretinal space, anterior changer, tear film of the eye.

Introducing the chosen biological sample to the antibody under conditions effective and for a period of time sufficient to allow the formation of immune complexes (primary immune complexes) is generally a matter of simply adding an antibody composition to the sample and incubating the mixture for a period of time lone enough for the antibodies to form immune complexes with, i.e., to bind to, any C3a, C3aR, C5a and/or C5aR present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

Immunoassays of the present invention which utilize the monoclonal antibodies are competitive and non-competitive immunoassays in either a direct or indirect format, forward, reverse, or simultaneous modes, including, the radioimmunoassay (RIA) and the sandwich (immunometric) assay and immunohistochemical assays on physiological samples. Those of skill in the art will know, or can readily discern, other immunoassay formats without undue experimentation.

The detection of immunocomplex formation is also well known in the art and may be achieved through the application of numerous approaches. These methods are generally based upon the detection of a label or marker, such as any radioactive, fluorescent, biological or enzymatic tags or labels known in the art. Exemplary U.S. patents concerning the use of such labels include U.S. Pat. Nos. 3,817,837; 3,850,752; 3,939,350; 3,996,345; 4,277,437; 4,275,149 and 4,366,241. The use of enzymes that generate a colored product upon contact with a chromogenic substrate are generally preferred. Secondary binding ligand, such as a second antibody or a biotin/avidin or biotin/streptavidin ligand binding arrangement, may also be used, as is known in the art.

The anti-C3a, anti-C3aR, anti-C5a, and/or anti-C5aR antibodies employed in the detection may themselves be operatively attached to a detectable label, wherein one would then simply detect this label, thereby allowing the amount of the primary immune complexes in the composition to be determined.

In one embodiment the primary immune complexes are detected by means of a second binding ligand that has binding affinity for the antibodies of the invention. In such cases, the second binding ligand may be operatively attached to a detectable label. The second binding ligand is itself often an antibody, and may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the first antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is operatively attached to a detectable label, allowing detection of the tertiary immune complexes thus formed. This system may provide for signal amplification if desired.

In the clinical diagnosis or monitoring of patients with an neovascular disease, the detection of C3a, C3aR, C5a, and/or C5aR, or an increase in the levels of C3a, C3aR, C5a and/or C5aR, in comparison to the levels in a corresponding biological sample from a normal subject is indicative of a patient with an neovascular disease.

However, as is known to those of skill in the art, such a clinical diagnosis would not likely be made on the basis of this method in isolation. Those of skill in the art are very familiar with differentiating between significant expression of a biomarker, which represents a positive identification, and low level or background expression of a biomarker. Indeed, background expression levels are often used to form a "cut-off" above which increased staining will be scored as significant or positive.

The in vivo diagnostic or imaging methods generally comprise administering or introducing to a patient a diagnostically effective amount of a C3a, C3aR, C5a and/or C5aR antibody that is operatively attached to a marker or label that is detectable by non-invasive methods. The antibody-marker conjugate is allowed sufficient time to localize and bind to C3a, C3aR, C5a and/or C5aR within the eye. The patient is then exposed to a detection device to identify the detectable marker, thus forming an image of the location of C3a, C3aR, C5a and/or C5aR in the eye of a patient. The presence of C3a, C3aR, C5a, C5aR or a combination thereof is detected by determining whether an antibody-marker binds to a component of the eye. Detection of or an increased level in C3a, C3aR, C5a, C5aR or a combination thereof in comparison to a normal individual without neovascular disease is indicative of a predisposition for and/or on set of neovascular disease. In a preferred embodiment of the invention there is provided an in vivo assay for detecting the presence of C3a, C3aR, C5a, or C5aR as a predisposition for or early detection of AMD. These aspects of the invention are also preferred for use in eye imaging methods and combined angiogenic diagnostic and treatment methods.

The anit-C3a, anti-C3aR, anti-C5a, and/or anti-C5aR antibodies or binding compounds or ligands for the in vivo detection of C3a, C3aR, C5a and/or C5aR, respectively, are given in a dose which is diagnostically effective. The concentration of detectably labeled antibody or compound which is administered should be sufficient such that the binding to C3a, C3aR, C5a, or C5aR and/or C3a-, C3aR-, C5a- and/or C5aR-bearing cells, is detectable compared to the background. Further, it is desirable that the detectably labeled antibody or compound be rapidly cleared from the circulatory system in order to give the best target-to-background signal ratio.

Dosages for in vivo imaging embodiments are generally less than for therapy, but are also dependent upon the age, gender, weight and extent of disease of a patient. One time doses should be sufficient. The dosage of the compound can vary from about 0.01 mg/kg to about 500 mg/kg, preferably about 0.1 mg/kg to about 200 mg/kg, most preferably about 0.1 mg/kg to about 10 mg/kg. Such dosages may vary, for example, depending on whether multiple injections are given, on the tissue being assayed, and other factors known to those of skill in the art.

For in vivo diagnostic imaging, the type of detection instrument available is a major factor in selecting an appropriate label or marker, like a radioisotope. The radioisotope chosen must have a type of decay which is detectable for the given type of instrument. Still another important factor in selecting a radioisotope for in vivo diagnosis is that the half-life of the radioisotope be long enough such that it is still detectable at the time of maximum uptake by the target, but short enough such that deleterious radiation with respect to the host is acceptable. Ideally, a radioisotope used for in vivo imaging will lack a particle emission but produce a large number of photons in the 140-250 keV range, which may be readily detected by conventional gamma cameras.

In antibody conjugates for in vivo diagnostic protocols markers or labels are required that can be detected using non-invasive methods. Many appropriate detectable markers or labels are known in the art, as are methods for their attachment to antibodies and binding ligands (see, e.g., U.S. Pat. Nos. 5,021,236 and 4,472,509). Examples of such labels include those that are, absorbant-based, chemiluminescent, fluorescent, nuclear magnetic spin-resonance, paramagnetic, radioactive, x-ray detectable, or a combination of the foregoing. Certain attachment methods involve the use of a metal chelate complex employing, for example, an organic chelating agent such a DTPA attached to the antibody (U.S. Pat. No. 4,472,509). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

An example of detectable labels are the paramagnetic ions. In this case, suitable ions include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred.

Ions useful in other contexts, such as X-ray imaging, include but are not limited to lanthanum (III), gold (III), lead (II), and especially bismuth (III). Fluorescent labels include rhodamine, fluorescein and renographin. Rhodamine and fluorescein are often operatively attached via an isothiocyanate intermediate.

In the case of radioactive isotopes for diagnostic applications, suitable examples include $^{14}$carbon, $^{51}$chromium, $^{36}$chlorine, $^{57}$cobalt, $^{58}$cobalt, copper$^{67}$, $^{152}$Eu, gallium$^{67}$, gallium$^{68}$, $^{3}$hydrogen, iodine$^{123}$, iodine$^{125}$, iodine$^{131}$, indium$^{113}$, indium$^{113}$, $^{59}$iron, mercury$^{197}$, mercury$^{203}$, $^{32}$phosphorus, rhenium$^{186}$, rhenium$^{188}$, rubidium$^{97}$, rubidium$^{103}$, $^{75}$selenium, $^{35}$sulphur, technetium$^{99m}$ and yttrium$^{90}$. $^{125}$I is often being preferred for use in certain embodiments, and technicium$^{99m}$ and indiun$^{111}$ are also often preferred due to their low energy and suitability for long range detection.

In the case of nuclear magnetic spin-resonance isotope, suitable examples include cobalt (II), copper (II), chromium (III), dysprosium (III), erbium (III), gadolinium (III), holmium (III), iron (II), iron (III), manganese (II), neodymium (III), nickel (II), samarium (III), terbium (III), vanadium (II) or ytterbium (III); or rhodamine or fluorescein.

Radioactively labeled C3a and/or C5a antibodies for use in the present invention may be produced according to well-known methods in the art. For instance, intermediary functional groups that are often used to bind radioisotopic metallic ions to antibodies are diethylenetriaminepentaacetic acid (DTPA) and ethylene diaminetetracetic acid (EDTA).

Monoclonal antibodies can also be iodinated by contact with sodium or potassium iodide and a chemical oxidizing agent such as sodium hypochlorite, or an enzymatic oxidizing agent, such as lactoperoxidase. Antibodies according to the invention may be labeled with technetium-99em by ligand exchange process, for example, by reducing pertechnate with stannous solution, chelating the reduced technetium onto a Sephadex column and applying the antibody to this column; or by direct labeling techniques, e.g., by incubating pertechnate, a reducing agent such as $SNCl_2$, a buffer solution such as sodium-potassium phthalate solution, and the antibody.

Any of the foregoing type of detectably labeled anti-C3a, anti-C3aR, anti-C5a and/or anti-C5aR antibodies may be used in the imaging or combined imaging and diagnostic aspects of the present invention. They are equally suitable for use in in vitro diagnostics.

In still another aspect, the present invention provides diagnostic kits, including both immunodetection and imaging kits, for use with the immunodetection and imaging methods described above. Accordingly, the anti-C3a, anti-C3aR, anti-C5a and/or anti-C5aR antibodies are provided in the kit, generally comprised within a suitable container.

For immunodetection, the antibodies may be bound to a solid support, such as a well of a microtitre plate, although antibody solutions or powders for reconstitution are preferred. The immunodetection kits preferably comprise at least a first immunodetection reagent. The immunodetection reagents of the kit may take any one of a variety of forms, including those detectable labels that are operatively attached to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being operatively attached to a detectable label. As noted above, a number of exemplary labels are known in the art and all such labels may be employed in connection with the present invention. These kits may contain antibody-label conjugates either in fully conjugated form, in the form of intermediates, or as separate moieties to be conjugated by the user of the kit.

The imaging kits will preferably comprise an antibody to C3a, C3aR, C5a and/or C5aR that is already attached to an in vivo detectable label. However, the label and attachment means could be separately supplied.

Either kit may further comprise control agents, such as suitably aliquoted compositions of C3a, C3aR, C5a and/or C5aR, whether labeled or unlabeled, as may be used to prepare a standard curve for a detection assay. The components of the kits may be packaged either in aqueous media or in lyophilized form.

The container means of the kits will generally include at least one vial, test tube, flask, bottle, syringe or other container means, into which the antibody or antigen may be placed, and preferably, suitably aliquoted. Where a second or third binding ligand or additional component is provided, the kit will also generally contain a second, third or other additional container into which this ligand or component may be placed. The kits may also include other diagnostic reagents for use in the diagnosis of any one or more neovascular diseases.

The kits of the present invention will also typically include a means for containing the antibody, and any other reagent containers in close confinement for commercial sale. Such containers may include injection or blow-molded plastic containers into which the desired vials are retained.

In another aspect of the invention there is provided a cell monitoring method utilizing the antibodies and compounds/ligands in vitro and in vivo to monitor the course of therapy for neovascular disease, like AMD. Thus, for example, by measuring the increase or decrease in the biological molecules associated with such a diseases or changes in the concentration of C3a, C3aR, C5a and/or C5aR, or C3a-, C3aR-, C5a- and/or C5a-bearing cells present in the eye or in various eye fluids, it would be possible to determine whether a particular therapeutic regimen aimed at ameliorating the AMD is effective.

EXAMPLES

The following examples are presented for the illustrative purposes and it is to be understood that the present invention is not limited to those precise embodiments. It should be appreciated by those of skill in the art that the techniques disclosed in the examples which follow represent techniques to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Animals

Male C3aR$^{-/-}$ and C5aR$^{-/-}$ mice, backcrossed 6 times to C57BL/6J, generated as described previously (Hopken, U. E., et al. (1996) *Nature* 383, 86-9; and Humbles, A. A., et al., (2000) *Nature* 406, 998-1001), and wild-type C57BL/6J mice (Jackson Labs) between 6 and 8 weeks of age were used to minimize variability. For all procedures, anesthesia was achieved by intramuscular injection of 50 mg/kg ketamine hydrochloride (Ft. Dodge Animal Health) and 10 mg/kg xylazine (Phoenix Scientific), and pupils were dilated with topical 1% tropicamide (Alcon).

Example 2

CNV

Laser photocoagulation (532 nm, 200 mW, 100 ms, 75 μm) (OcuLight GL, Iridex) was performed (volume studies: 3/eye; protein analyses/flow cytometry: 12/eye) on both eyes of each animal to induce CNV as previously described in Sakurai, E., Taguchi, H., Anand, A., Ambati, B. K., Gragoudas, E. S., Miller, J. W., Adamis, A. P. & Ambati, J. (2003) *Invest Ophthalmol Vis Sci* 44, 2743-9; and Sakurai, E., Anand, A., Ambati, B. K., van Rooijen, N. & Ambati, J. (2003) *Invest Ophthalmol Vis Sci* 44, 3578-85. CNV volumes were measured by scanning laser confocal microscope (TCS SP, Leica) as previously reported (Id.) with 0.5% FITC-*Griffonia simplicifolia* Isolectin B4 (Vector Laboratories) or 0.5% FITC-rat antibody against mouse CD31 (BD Pharmingen). Volumes obtained by lectin and CD31 staining were highly correlated ($r^2$=0.95).

Example 3

Complement Inhibition

The C3a receptor antagonist (C3aRA) N$^2$-[(2,2-diphenylethoxy)acetyl]-arginine (Ames, R. S., Lee, D., Foley, J. J., Jurewicz, A. J., Tornetta, M. A., Bautsch, W., Settmacher, B., Klos, A., Erhard, K. F., Cousins, R. D., Sulpizio, A. C., Hieble, J. P., McCafferty, G., Ward, K. W., Adams, J. L., Bondinell, W. E., Underwood, D. C., Osborn, R. R., Badger, A. M. & Sarau, H. M. (2001) *J Immunol* 166, 6341-6348) and C5a receptor antagonist (C5aRA) AcF[OPdChaWR] (Finch, A. M., Wong, A. K., Paczkowski, N. J., Wadi, S. K., Craik, D.

J., Fairlie, D. P. & Taylor, S. M. (1999) *J Med Chem* 42, 1965-74), were synthesized as previously described (Reca, R., Mastellos, D., Majka, M., Marquez, L., Ratajczak, J., Franchini, S., Glodek, A., Honczarenko, M., Spruce, L. A., Janowska-Wieczorek, A., Lambris, J. D. & Ratajczak, M. Z. (2003) *Blood* 101, 3784-93; Mastellos, D., Papadimitriou, J. C., Franchini, S., Tsonis, P. A. & Lambris, J. D. (2001) *J Immunol* 166, 2479-86). A nonsense peptide (IAVVQD-WGHHRAT), synthesized as described previously (Sahu, A., Soulika, A. M., Morikis, D., Spruce, L., Moore, W. T. & Lambris, J. D. (2000) *J Immunol* 165, 2491-9), was used as control. Rat IgG2a antibody against mouse C3a (clone 3/11; Hycult Biotechnology), which inhibits C3a activity (unpublished data, J.D.L.), and rabbit polyclonal IgG antibody against a synthetic peptide constructed from the carboxyl-terminal region of rat C5a (Huber-Lang, M. S., Sarma, J. V., McGuire, S. R., Lu, K. T., Guo, R. F., Padgaonkar, V. A., Younkin, E. M., Laudes, I. J., Riedemann, N. C., Younger, J. G. & Ward, P. A. (2001) *FASEB J* 15, 568-70), which also inhibits mouse C5a (unpublished data, J.V.S.), and were used to block C3a and C5a. Rabbit IgG and rat IgG2a (Jackson Immunoresearch) were used as controls. These reagents were injected into the vitreous humor of wild-type mice using a 33-gauge Hamilton syringe either immediately after or three days after laser injury.

Example 4

Immunohistochemistry

Frozen sections fixed in Histochoice MB (Amresco) and blocked with 5% donkey serum (Jackson Immunoresearch) were stained with chicken antibodies against mouse C3 (1:750) or C5 (1:5,000; both gifts of S. R. Barnum, University of Alabama, Birmingham). Bound antibody was detected with Cy3-donkey secondary (1:750; Jackson Immunoresearch). Rabbit antibody against mouse RPE65 (1:1,000; gift of M. Redmond, National Eye Institute, Bethesda) in conjunction with Alexa 488-donkey secondary (1:200; Molecular Probes) was used to localize RPE cells. Cell nuclei were stained with 4',6'-diamino-phenylindole (DAPI; Molecular Probes).

Example 5

Cell Culture

Human RPE cells (gift of David R. Hinton, University of Southern California) were cultured in Dulbecco's modified essential medium (Invitrogen) containing 10% fetal bovine serum, penicillin G (100 U/ml), streptomycin sulfate (0.1 mg/ml) (all from Sigma-Aldrich) at 37° C. under 10% $CO_2$ and 90% room air. Cells were used for experiments upon attaining 80% or 100% confluence.

Example 6

VEGF ELISA

The RPE/choroid complex was dissected from the mouse eye and sonicated in lysis buffer (20 mM imidazole HCl, 10 mM KCl, 1 mM $MgCl_2$, 10 mM EGTA, 1% Triton X-100, 10 mM NaF, 1 mM Na molybdate, 1 mM EDTA with protease inhibitor (Sigma-Aldrich)) on ice for 45 sec. VEGF protein levels (pg/ml) in the RPE cell culture supernatant or the RPE/choroid lysate were determined by ELISA (R&D Systems) and normalized to total protein (µg/ml) (Bio-Rad).

Example 7

Western Blotting

Equal amounts of total protein from RPE/choroid were resolved in SDS 4-20% polyacrylamide gradient gel and transferred to nitrocellulose membranes for western blotting with chicken antibodies to mouse C3 or mouse C5 (1:100; gift of S. R. Barnum, University of Alabama, Birmingham). Equal loading was assessed by blotting with rabbit antibody to human GAPDH (1:2,000; Abcam).

Example 8

Flow Cytometry

Single cell suspensions isolated from mouse RPE/choroids via collagenase D treatment (20 U/mL; Roche Diagnostics) were incubated in Fc block (0.5 mg/mL; BD Pharmingen) for 15 min on ice, stained with Cy5-rat antibody to mouse F4/80 (1:30; Serotec), FITC-hamster antibody to mouse CD11c (1:100; Serotec), or PE-rat antibody to mouse Gr-1 (1:200; eBioscience), and subjected to FACS analysis (FACScalibur, BD Biosciences). Macrophages and neutrophils were defined as F4/80+CD11c- and Gr-1+F4/80-cells, respectively.

Example 9

Statistics—Volume of CNV

Because the probability of each laser lesion developing CNV is influenced by the group to which it belongs, the mouse, the eye, and the laser spot, the mean lesion volumes were compared using a linear mixed model with a split plot repeated measures design, as previously described. Id. The whole plot factor was the genetic group to which the animal belonged while the split plot factor was the eye. Statistical significance was determined at the 0.05 level. Post hoc comparison of means was constructed with a Bonferroni adjustment for multiple comparisons.

Example 10

Protein Levels and Flow Cytometry

VEGF protein data are represented as the mean±s.e.m. of at least 3 independent experiments and compared using a two-tailed Student's t-test. The null hypothesis was rejected at $P<0.05$.

Example 11

Diagnostic Assay

Anti-C3a, anti-C3aR, anti-C5a and/or anti C5aR antibodies are labeled with fluorescein, indocyanine green, or conjugates thereof. The labeled antiC3a and C5a antibodies or Fab fragments thereof are injected into the vitreous humor of the eye or intravenously and detected by fluorescent imaging using appropriate excitation and emission filters through a dilated pupil.

What is claimed is:

1. A pharmaceutical composition for treating and/or preventing choroidal neovascularization (CNV) comprising, a therapeutically effective amount of an antibody that binds selectively to the receptor of C3a (C3aR), and prevents choroidal neovascularization and an ophthalmically acceptable pharmaceutical carrier, wherein the antibody comprises a pharmaceutical agent operatively attached thereto.

2. The composition according to claim 1 wherein the pharmaceutical agent is an anti-inflammatory agent.

3. The composition of claim 1 wherein the pharmaceutical agent is a radioisotope.

4. The composition of claim 3 wherein the radioisotope is $^{211}$Astatine or $^{131}$Iodine.

5. The composition of claim 1 wherein said composition is formulated for intravitreous injection.

* * * * *